United States Patent
Thompson (10) Patent No.: US 7,452,336 B2
(45) Date of Patent: Nov. 18, 2008

(54) INTERACTIVE NEURAL TRAINING DEVICE

(75) Inventor: James W. Thompson, Carmichael, CA (US)

(73) Assignee: Interactive Neuro Technology, Inc., Sacramento, CA (US)

( * ) Notice: Subject to any disclaimer, the term of this patent is extended or adjusted under 35 U.S.C. 154(b) by 140 days.

(21) Appl. No.: 10/934,347

(22) Filed: Sep. 3, 2004

(65) Prior Publication Data

US 2005/0065452 A1    Mar. 24, 2005

Related U.S. Application Data

(60) Provisional application No. 60/500,466, filed on Sep. 6, 2003.

(51) Int. Cl.
| | |
|---|---|
| *A61B 5/00* | (2006.01) |
| *A61B 5/04* | (2006.01) |
| *A61B 5/103* | (2006.01) |
| *A61B 5/117* | (2006.01) |
| *A61B 3/00* | (2006.01) |
| *A61N 1/00* | (2006.01) |

(52) U.S. Cl. .................. 600/558; 600/559; 600/544; 600/545; 600/587; 600/595; 607/2; 607/45; 607/53; 607/54; 607/59; 607/60; 607/62; 351/203

(58) Field of Classification Search ............ 600/558, 600/559, 544, 545, 587, 595; 607/2, 45, 607/53, 54, 59, 60, 62; 351/203
See application file for complete search history.

(56) References Cited

U.S. PATENT DOCUMENTS

| | | | |
|---|---|---|---|
| 3,024,020 A | * | 3/1962 | Alton ........................... 482/8 |
| 3,503,608 A | | 3/1970 | Ylinen |
| 3,933,354 A | | 1/1976 | Goldfarb et al. |
| 4,058,113 A | | 11/1977 | Fields |
| 4,261,563 A | | 4/1981 | Goldfarb |
| 4,285,517 A | | 8/1981 | Morrison |
| 4,824,237 A | * | 4/1989 | Ratner et al. ................ 351/203 |
| 4,978,303 A | | 12/1990 | Lampbell |
| 5,009,419 A | | 4/1991 | Streeter |
| 5,204,813 A | * | 4/1993 | Samph et al. ............... 434/362 |
| 5,289,389 A | * | 2/1994 | Keller ......................... 702/116 |
| 5,295,491 A | * | 3/1994 | Gevins ........................ 600/544 |
| 5,303,327 A | * | 4/1994 | Sturner et al. ............... 704/270 |
| 5,522,386 A | * | 6/1996 | Lerner ........................ 600/547 |
| 5,613,690 A | * | 3/1997 | McShane et al. ............ 273/449 |
| 5,615,123 A | * | 3/1997 | Davidson et al. ............ 700/233 |
| 5,682,882 A | * | 11/1997 | Lieberman .................. 600/301 |
| 6,066,105 A | * | 5/2000 | Guillen ........................ 600/595 |
| 6,081,750 A | * | 6/2000 | Hoffberg et al. .............. 700/17 |
| 6,110,073 A | * | 8/2000 | Saur et al. ....................... 482/8 |
| 6,113,538 A | * | 9/2000 | Bowles et al. ............... 600/300 |

(Continued)

*Primary Examiner*—Max Hindenburg
*Assistant Examiner*—Jeffrey G Hoekstra
(74) *Attorney, Agent, or Firm*—John P. O'Banion (57) ABSTRACT

An apparatus and method for rehabilitating patients and assessing tactile skills in response to visual stimuli generated from a portable neural training device. The device generates a visual output to elicit tactile response (hand movement) from the patient. The device preferably automatically adjusts the difficulty of a session in response to demonstrated patient skill level (i.e. combination of correct responses, speed, and accuracy of responses). The invention evaluates and challenges the patient to control tactile response, overcome visual perception difficulties, or practice simple multi-tasking or reasoning skills. The invention also provides information which is valuable to those administering the rehabilitation program or assessing patient skill and/or progress. By way of example the neural training device is described with an embodiment having discrete fixed keys and an embodiment utilizing a touch sensitive display screen.

11 Claims, 9 Drawing Sheets

U.S. PATENT DOCUMENTS

| | | | |
|---|---|---|---|
| 6,191,774 B1* | 2/2001 | Schena et al. | 345/163 |
| 6,261,239 B1* | 7/2001 | Abraham-Fuchs et al. | 600/558 |
| 6,262,717 B1* | 7/2001 | Donohue et al. | 345/173 |
| 6,371,931 B1* | 4/2002 | Guillen | 600/595 |
| 6,436,058 B1* | 8/2002 | Krahner et al. | 600/587 |
| 6,485,417 B1* | 11/2002 | Bowles et al. | 600/300 |
| 6,632,174 B1* | 10/2003 | Breznitz | 600/300 |
| 6,648,834 B2* | 11/2003 | Kajimoto et al. | 600/558 |
| 6,719,690 B1* | 4/2004 | Cassily | 600/300 |
| 6,720,860 B1* | 4/2004 | Narayanaswami | 340/5.54 |
| 2001/0028361 A1* | 10/2001 | Culver | 345/701 |
| 2001/0040553 A1* | 11/2001 | Rosenberg | 345/158 |
| 2001/0046893 A1* | 11/2001 | Giobbi et al. | 463/24 |
| 2002/0005111 A1* | 1/2002 | Ludwig | 84/645 |
| 2002/0022551 A1* | 2/2002 | Watterson et al. | 482/8 |
| 2002/0030664 A1* | 3/2002 | Schena et al. | 345/163 |
| 2002/0039923 A1* | 4/2002 | Cannon et al. | 463/42 |
| 2002/0055384 A1* | 5/2002 | Armstrong | 463/37 |
| 2002/0068605 A1* | 6/2002 | Stanley | 455/556 |
| 2002/0083025 A1* | 6/2002 | Robarts et al. | 706/12 |
| 2002/0132216 A1* | 9/2002 | Dohrmann | 434/362 |
| 2003/0009270 A1* | 1/2003 | Breed | 701/29 |
| 2003/0060729 A1* | 3/2003 | Leyva et al. | 600/558 |
| 2003/0085870 A1* | 5/2003 | Hinckley | 345/156 |
| 2003/0135127 A1* | 7/2003 | Sackner et al. | 600/536 |
| 2003/0144711 A1* | 7/2003 | Pless et al. | 607/60 |
| 2003/0181822 A1* | 9/2003 | Victor | 600/558 |
| 2003/0193572 A1* | 10/2003 | Wilson et al. | 348/207.99 |
| 2003/0228906 A1* | 12/2003 | Walker et al. | 463/40 |
| 2004/0008191 A1* | 1/2004 | Poupyrev et al. | 345/184 |
| 2004/0019370 A1* | 1/2004 | Gliner et al. | 607/48 |
| 2004/0039509 A1* | 2/2004 | Breed | 701/45 |
| 2004/0056877 A1* | 3/2004 | Nakajima | 345/702 |
| 2004/0059249 A1* | 3/2004 | Kajimoto et al. | 600/558 |
| 2004/0087843 A1* | 5/2004 | Rice et al. | 600/319 |
| 2004/0104941 A1* | 6/2004 | Natoli | 345/772 |
| 2004/0122486 A1* | 6/2004 | Stahmann et al. | 607/60 |
| 2004/0215286 A1* | 10/2004 | Stypulkowski | 607/48 |
| 2004/0254501 A1* | 12/2004 | Mault | 600/587 |
| 2005/0192513 A1* | 9/2005 | Darby et al. | 600/558 |

* cited by examiner

Response Mode — Skill Level 1 — 16 Blocks Active

FIG. 3

Responsive Mode − Skill Level 2 − Example "a" − 8 Blocks Active

FIG. 4

Responsive Mode − Skill Level 2 − Example "b" − 8 Blocks Active

FIG. 5

Responsive Mode — Skill Level 3 — Example "a" — 4 Blocks Active

FIG. 6

Responsive Mode — Skill Level 3 — Example "b" — 4 Blocks Active

FIG. 7

Responsive Mode — Skill Level 3 — Example "c" — 4 Blocks Active

FIG. 8

Responsive Mode — Skill Level 4 — 1 Block Active

FIG. 9

Responsive Mode — Skill Level 5 — 1 1/2" Square

FIG. 10

Visual Perception Mode — Example "a"

FIG. 11

Visual Perception Mode – Example "b"

FIG. 12

Visual Perception Mode – Example "c"

FIG. 13

Visual Perception Mode — Example "d"

FIG. 14

Predictive Mode — Skill Level 1 — Example "a"
Moving Target Area: 2 1/2" x 2 1/2"

FIG. 15

Predictive Mode — Skill Level 1 — Example "b"
Moving Target Area: 2 1/2" x 2 1/2"

FIG. 16

Multi-Task Mode

FIG. 17

INTERACTIVE NEURAL TRAINING DEVICE

CROSS-REFERENCE TO RELATED APPLICATIONS

This application claims priority from U.S. provisional application Ser. No. 60/500,466 filed on Sep. 6, 2003, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to interactive training devices, and more particularly to a neurological trainer for patient rehabilitation and assessments.

2. Description of Related Art

Neurological disorders affect an increasing segment of the population as the average age of the population increases. The cause of neurological disorders can stem from accidents, diseases, or conditions typically attributed to advanced age, such as strokes, Alzheimer's disease, and so forth. Those suffering with neural disorders often have a diminished quality of life. A substantial amount of research is being performed in these areas toward mitigating the loss of patient mental and physical function.

The National Institute of Neurological Disorders and Stroke (NINDS), a component of the Federal Government's National Institutes of Health (NIH), has primary responsibility for sponsoring research on disorders of the brain and nervous system, including the acute phase of stroke and the restoration of function after stroke. NINDS also supports research on ways to enhance repair and regenerate the central nervous system.

Scientists funded by NINDS are studying how the brain responds to experience or adapts to injury by reorganizing its functions (plasticity) by using noninvasive imaging technologies to map patterns of biological activity inside the brain. Other NINDS-sponsored scientists are looking at brain reorganization after stroke and determining whether specific rehabilitative techniques, such as constraint-induced movement therapy and transcranial magnetic stimulation, can stimulate brain plasticity to improve motor function and decrease disability. Other scientists are experimenting with implantation of neural stem cells to determine if these cells can replace cells that have died as a result of a stroke.

Research information collected by the National Institute of Neurological Disorders and Stroke (NINDS) provides strong indication of the efficacy of utilizing neural stimulation to aid victims of neurological disorders such as strokes, Alzheimer's disease, and so forth.

A consensus is being reached that one of the most important elements of any rehabilitation program is carefully directed, well-focused, repetitive practice. Some consider that the best forms of practice are those most similar to those utilized by persons in learning a new skill, such as playing the piano, using a computer keyboard, or pitching a baseball. It is becoming a more widely-held view that repetitive use of impaired limbs encourages brain plasticity, which is the organizational adaptability of the brain in response to damage, while helping to reduce disabilities.

A recent trend in physical therapy involves engaging the patient in goal-directed activities, such as playing games, to promote coordination. Physical therapists often employ mechanisms for providing sensory stimulation to encourage use of impaired limbs while aiding patients toward regaining abilities and awareness of stimuli. One technique employed by physical therapists is that of restraining a more operable limb while practicing motor skills tasks with the impaired limb in order to encourage its use and provide rehabilitation.

In addition, a number of problems with thinking and memory can arise in stroke survivors that develop apraxia wherein they lose their ability to plan and carry out the steps of a plan in the proper sequence. In addition, stroke survivors often have problems following a set of instructions. It appears that apraxia is caused by some disruption of the subtle connections that exist between thought and action.

Accordingly a need exists for a system and method of providing sensory stimulation coupled with coordinated motor activity, and providing assessment thereof. These needs and others are met within the present invention, which overcomes the deficiencies of previously developed rehabilitation devices and methods.

BRIEF SUMMARY OF THE INVENTION

A system and method are described for rehabilitating victims of strokes, Alzheimer's disease, or other neurological disorders. The system also provides for assessing and evaluating neurological disorders, such as within a patient rehabilitation regime.

The invention elicits tactile response from a user interacting with visual stimuli preferably generated by the device from a two-dimensional key array. By way of example, the tactile responses are collected by keys which are configured to generate a visual stimulus according to a means of visual annunciation, such as illuminating, changing color or shade, or a combination of visual attribute changes. One preferred form of visual annunciation is provided in response to activating at least one light emitting diode (LED). The tactile inputs may be arranged in a desired pattern, such as a square planar grid, or configured under program control. The neural training device may comprise physical keys which are configured to provide a visual stimuli associated with each given key, or the device may comprise a touch-sensitive display having portions demarcated as keys and upon which a visual stimuli is displayed to elicit a user response.

The neural training device provides a number of significant advantages. The device is easy to use by nearly any age group and does not create any language skill barrier, or barrier to those that are hearing impaired. The device supports exercise sessions of any desired duration. The construction of the device provides portability and it can be implemented with a robust construction that is not readily damaged by dropping, liquid spills, contaminants, or other harsh conditions of use.

The interactive neural training device is designed to assist the therapist in the neurological rehabilitation and assessment of patients. In the rehabilitation process desired patient activities with the device can be readily configured by the therapist for specific patient needs and skill levels. The device is designed to readily accommodate the unassisted patient, for example in the home environment. In addition, it is designed to supplement current therapeutic training devices and methods that are utilized in the clinical environment. The system is designed to be preferably left with the patient for an extended period of time, allowing for several minutes or hours of practice per day without the need of direct supervision from a health professional. During these practice sessions, the device programming attempts to optimize patient progress by continuously monitoring progress on the exercise, or exercises, and adjusting the level of challenge to match patient capability.

In performing assessment and evaluation with the neural training device, the therapist can use the device as a one-on-one assessment tool during regular visitations by taking advantage of its ability to precisely measure patient responses to various visual stimuli. Optionally, the neural training device can be configured with one or more inputs to allow selecting either a practice mode or specific evaluation mode. The therapist can also evaluate long term patient progress by analyzing scores that have been averaged and stored in memory over a period of time, such as over several weeks.

A number of response patterns can be created with the invention to be followed by the patient. The device both generates a visual stimulus to which the patient is to respond and measures the accuracy and timing of the patient responses. In a preferred embodiment of the invention a display is provided upon which the results for a given interaction session, cumulative totals, or other information can be displayed. In addition, for more advanced patient training in an optional mode, the display can be utilized as a means for generating textual instructions to which the patient is to provide a tactile response.

To assess the accuracy of tactile response, each tactile response sensor (i.e. key) can be configured according to the invention with a means to correlate how accurately the tactile feedback corresponds with the visual stimuli. For example, a tactile feedback sensor may be implemented as a nested form of key in which an "inner key" is surrounded by an "outer key". The accuracy of key presses thus can be detected by determining how sloppy the interaction is with regard to pressing the proper "inner key" as opposed to the "outer key" in response to the visual stimuli (or in some instances the converse action).

The goals of the invention are generally to provide visual stimuli to a patient to stimulate motor skill interactivity, monitor the progress of patient interaction, and to adjust the difficulty of the visual stimulus and motor skill response based on the feedback provided by the patient. In one mode, the invention evaluates and challenges patient ability to control hand movement. In another mode, the invention assists a patient to identify and overcome deficiencies with visual perception. In another mode, the invention assists the user to practice reasoning skills. In still another mode, the invention provides exercises that are designed to assist the patient in the development of multi-tasking skills.

In one embodiment, the invention comprises: (a) means for providing visual stimuli to a user; (b) means for receiving tactile feedback from the user in response to the visual stimuli; and (c) means for controlling presentation of the visual stimuli to the user and for processing the tactile feedback.

In a more detailed embodiment the apparatus comprises a touch pad that has a plurality of primary touch sensitive keys arranged in a matrix. Each primary key has a secondary touch sensitive key positioned in the approximate center thereof, and each secondary key has a light emitting source positioned approximately in its center. The apparatus includes a microprocessor and associated programming for providing visual stimuli to a user, monitoring tactile feedback from the user in response to the visual stimuli, controlling presentation of the visual stimuli to the user, and processing the tactile feedback.

In one mode, the apparatus generates one or more patterns of visual stimuli, enables one or more of the touch sensitive keys to be responsive to tactile feedback from the user in response to the visual stimuli, and alters the number and position of touch sensitive keys which are responsive to tactile feedback from the user.

In another mode, control parameters for the device, or programming, can be received through an external communication means, which for example may be implemented as an optical link, wireless data link, wired data link and so forth.

In another mode, the apparatus provides the visual stimuli, measures response time and precision of tactile feedback from the user, and adjusts the number and position of the touch sensitive keys based on user responses (skill level).

In another mode, the apparatus illuminates first and second adjacent touch sensitive keys, wherein one of the keys is illuminated continuously and an adjacent key is illuminated intermittently. Tactile feedback from the user in response to illumination of the first and second adjacent touch sensitive keys is monitored, and audible feedback is provided to the user if the user touches a touch sensitive key adjacent to the intermittently illuminated touch sensitive key.

In another mode, the apparatus provides visual stimuli, receives tactile feedback from the user, provides a first type of audible feedback to the user in response to receiving the tactile feedback from the user, and provides a second type of audible feedback to the user in response to receiving tactile feedback from the user. The first type of audible feedback is provided in response to tactile feedback applied to individual touch keys. The second type of audible feedback is provided in response to tactile feedback applied to a predetermined number of the touch keys.

In still another mode, the apparatus provides visual stimuli to be responded to by tactile feedback from both hands of the user to develop multi-tasking skill.

In one embodiment the invention can be described as an apparatus for performing neural training and assessment, comprising: (a) a plurality of touch sensitive areas configured for detecting user tactile input; (b) a pair of sense bars for passively restraining a limb; (c) a plurality of visual indicators configured for being associated with each of the touch sensitive areas; and (d) a control circuit configured for activating one or more visual indicators as a tactile stimulus and registering user accuracy and speed in response to tactile contact by the user within the plurality of touch sensitive areas as qualified by detection that user contact is maintained on a specific sense bar from the pair of sense bars. The touch sensitive areas can be provided as separate keys and associated visual indicators, or as touch sensitive areas on a touch sensitive display screen. In either case the touch sensitive areas can be configured to provide a tactile stimulus of a desired size according to skill level.

Another embodiment of the invention is a method for assisting in the evaluation and rehabilitation of neurological impairments. In this embodiment, visual stimuli is presented to a user, tactile feedback from the user in response to the visual stimuli is monitored, and presentation of the visual stimuli to the user is controlled in response to the tactile feedback. This embodiment is carried out using the apparatus described above, and the modes of operation also described above.

One embodiment of the invention provides four modes of device operation including a responsive mode, visual perception mode, predictive mode and a multi-task mode. In the responsive mode random stimulus/response patterns are provided with multiple levels of challenge to accommodate a wide range of patient needs. The device elicits patient response as the patient follows the random visual stimuli. The visual perception mode generally provides light patterns that aid a user in overcoming spatial visual dysfunction, such as in discerning responses to left/right or top/bottom stimuli and the associated motor responses. In predictive mode light sequences are generated to help in the prediction of a sequence of events. The user is not just matching their motor response to the visual stimuli but must predict the correct motor response based on the visual stimuli. In the multi-task mode, randomly changing visual stimuli are separately displayed for both the right and left hands. The patient is elicited to respond to the two visual stimuli using both hands, wherein the position of the stimuli for one hand changes independently from the position of the stimuli for the other. It will be appreciated that combinations and variations of the above patterns can be created by one of ordinary skill in the art based on the teachings herein without departing from the present invention.

All modes of interaction are preferably configured for automatically adjusting the degree of challenge, such as according to discrete skill levels, as appropriate. The programming within the device is configured to monitor the responses of the patient with regard to how those responses match up with the selected degree of challenge. The unit therefore can increase or decrease challenge to keep the patient stimulated without overtaxing, or under stimulating, the patient. The system is preferably configured to register both motor skill response time and "precision" of response.

In one embodiment of the invention patient response data is averaged and stored in memory at frequent intervals, such as over a period of several days of unsupervised training exercise. This long-term information can be made available non-exclusively, allowing the patient and others to access the data. The availability of the information may also be accessed on a restricted basis, such as to the therapist or other medical practitioner overseeing the rehabilitation.

An option is provided in which one limb, is "restrained" to selectively rehabilitate and evaluate patient use of the other limb. In a preferred embodiment, the system provides for restraining the patient without cumbersome straps and so forth, such as by relying on sensing the location of a limb on a contact area, for example the hand of the user being retained upon an area of the device.

Separate scores are recorded for patient time of response for activities in each of four visual quadrants on the trainer surface. This recorded data is available to the therapist. Recorded data that can be made available include: total practice time, total number of practice sessions, skill level achievements, average response time for all responses, average response time for each given area (i.e. in each of the four quadrants), average results for precision of hand movement, and other measurements that can be determined from the interaction data.

In one embodiment of the system data can be uploaded or downloaded from the system or to the system. Recorded data can be uploaded, such as to a database of a medical practitioner (i.e. therapist), or to otherwise provide additional data storage as well as analysis, results graphing and the like. Programming, including the use of new or custom patterns can be downloaded into the system. In addition the communication link can be utilized for testing the device or gathering diagnostic information.

A number of inventive aspects are described for the present invention which include but are not limited to the following.

An aspect of the invention is to provide for neurological training and assessment of motor responses to visual stimuli.

Another aspect of the invention is to provide a variety of training patterns which can be directed at specific rehabilitation challenges.

Another aspect of the invention is to provide a mechanism for testing specific limb function without the need of relying on physical restraint straps or similar devices.

Another aspect of the invention is to provide a variety of training levels wherein the patient can be constantly challenged without being overwhelmed or under stimulated.

Another aspect of the invention is to provide automatic adjustment of training level based on registration and device assessment of user capabilities.

Another aspect of the invention is to provide a portable training device that can tolerate rough handling and harsh environments.

Another aspect of the invention is to provide a neurological training device configured for uploading session data to another system, or to download different programming, patterns, control parameters, and so forth into the neural training device.

Another aspect of the invention is to provide a neurological training device which registers both the speed and accuracy of user response.

Another aspect of the invention is to provide a neurological training device which records activity within each user practice session and is capable of generating statistics on performance.

Another aspect of the invention is to provide a portable neural training device that can be used by the unsupervised patient in a home environment.

A still further aspect of the invention is to provide a neural training device that can be manufactured at reasonable cost and widely deployed.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 17. It will be appreciated that the apparatus may vary as to configuration and as to details of the parts, and that the method may vary as to the specific steps and sequence, without departing from the basic concepts as disclosed herein.

1. Embodiment of Neural Trainer Hardware.

The neural training device described herein is a portable, hand held, tool designed to assist in the evaluation and rehabilitation of individuals with learning disabilities or neurological impairments such as, but not limited to, those resulting from stroke, Alzheimer's disease, and other afflictions. Although the device can be implemented in a number of alternative ways, two primary input/output hardware configurations are described. The first configuration is described as having discrete input/output (I/O) while the second is said to provide programmed I/O.

The discrete I/O implementation utilizes discrete elements to generate the visual stimuli and to sense the tactile responses. For example, discrete keys can be utilized for registering user interaction, with the visual stimuli being provided as indicators contained on, or proximal to, the keys. The programmed tactile I/O implementation relies upon a touch-sensitive display upon which the location of tactile inputs is displayed (i.e. displaying key legends or outlines of keys). The programming in this case determines the position of the tactile inputs as well as their appearance. Combinations of the discrete and programmed I/O implementations may also be implemented without departing from the teachings of the present invention.

Figure 1:
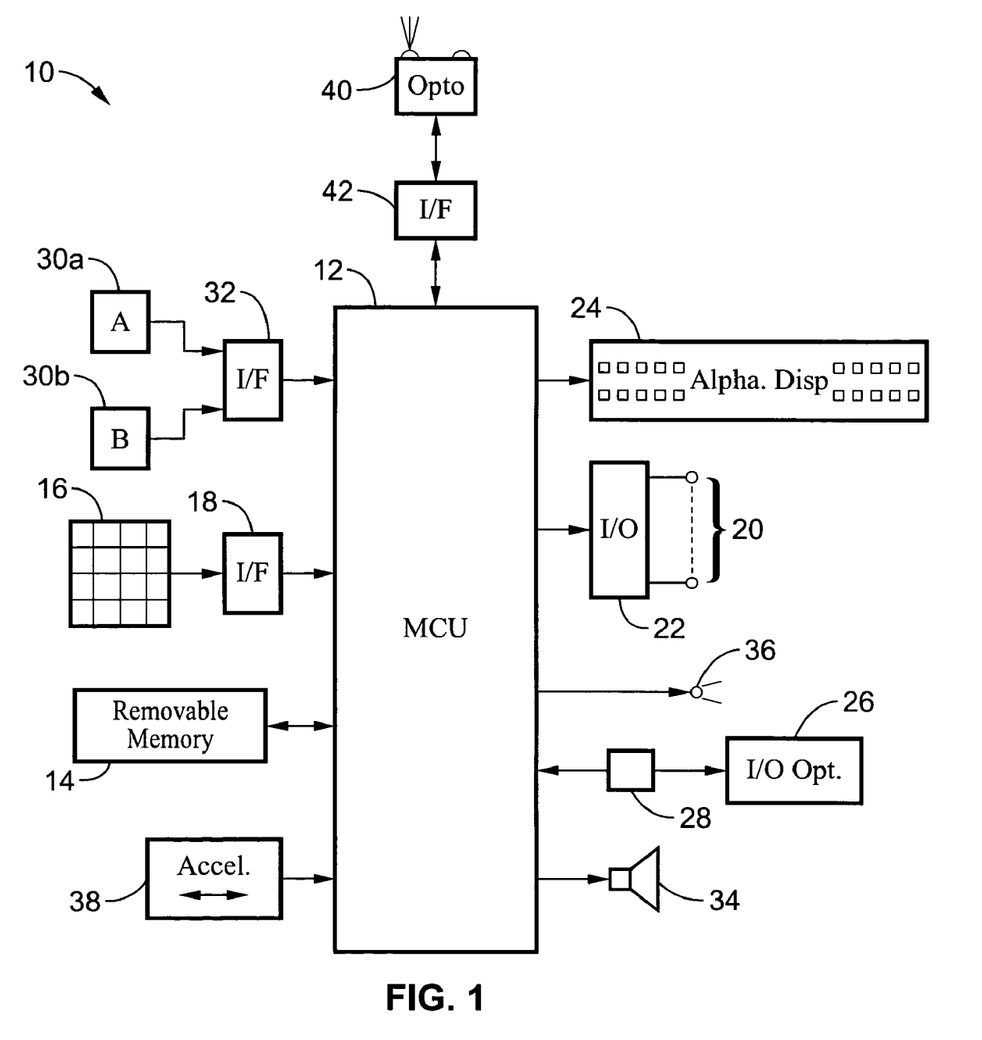
FIG. 1 is a block diagram of a neural training device according to an embodiment of the present invention, showing the input and output elements of the device coupled to a microcontroller.

FIG. 1 illustrates an example embodiment of the neural training device 10 according to the discrete I/O implementation. A controller 12 preferably comprises a microcontroller which is shown in this case having internal RAM memory. According to one implementation the microcontroller can comprise an inexpensive microcontroller (i.e. PIC16LF877 from Microchip® Corporation of Chandler, Ariz.) to control system functions. The program code in this example preferably resides in Flash memory within controller 12, although other forms of non-volatile storage may be utilized such as E²PROM, ROM and so forth. Additionally, test result data may be collected by the system during user operation, such as is stored in non-volatile memory within, or coupled to, the microcontroller.

In one embodiment the memory can include the use of non-volatile memory 14, such as a memory stick, memory module, or the like for retaining session statistics, as well as for establishing the training parameters for a given patient. By way of example user response information can be stored as response time averages determined for specific periods of device use, such as every n number of minutes of trainer device operation (i.e. n=15). The memory chip can be removed for reading its retained data on a data collection system, for example which may provide for charting of user progress. The neural training device is preferably configured with sufficient memory for storing results over a short period, such as during the interval between when the memory chip is removed and sent for download, and when another memory chip is inserted. Once the memory chip is reinstalled, the temporary data is then transferred into the memory chip.

Those skilled in the art will appreciate that many of the features and functions of the invention are embodied in software executable by the microcontroller, and that those functions can be implemented using conventional programming techniques. Furthermore, the hardware can be implemented using integrated circuits, discrete components, application specific integrated circuits (ASICS) and other conventional components and techniques.

Power to the neural-trainer device can be provided by any convenient method, such as batteries, capacitors, AC adapters, as well as other methods of supplying operating power. In a preferred embodiment power is provided to the unit by a battery pack consisting of six NiMh batteries having a nominal output of 7.2 V and having a sufficient operating capacity (i.e. ranging from 500 mAh-2000 mAh). It is estimated that utilizing a battery capacity toward the larger end of that range will allow active operation of the trainer for at least 20 continuous hours. The device is configured for recharging the batteries via an AC charge adapter or other charging mechanism. Preferably, the microcontroller is configured with a means of sensing battery condition and outputs an audio or visual indication, or both, in response to the low battery condition.

User tactile sensory inputs are depicted as a group of thirty two nested keys 16 coupled through a keypad interface circuit 18. The keys are preferably configured as sixteen touch sensitive inner keys, each surrounded by an outer key area which is also touch sensitive. The inner-outer configuration of the keys provides a mechanism for sensing the accuracy of user responses. It should be appreciated that the device can be configured with more or fewer keys as desired.

In one embodiment the thirty two key matrix (16 inner and 16 outer keys) comprises the primary user interface within this embodiment of the device and it can be implemented in a number of alternative ways. By way of example, the keyboard matrix can be created by etching around the keys on the surface of a printed circuit board that is attached to and controlled by key control circuitry 18 comprising a key panel proximity sensor (i.e. Quantum® part number QT60326-AS as produced by Quantum Research Group of Southhampton, Hants in the United Kingdom or similar), that interfaces with the microcontroller. The key control circuit is preferably configured in this embodiment to allow the microcontroller to read data from, or send control codes to, the key control circuit. The control codes allow microcontroller 12 to adjust the operational characteristics of the key panel controller and characteristics of the keyboard "on the fly".

A set of key indicators 20 is shown for being driven by output interface 22 (i.e. multi-character LED lamp driver such as Motorola® part number MC14489BP or similar). In one embodiment of the invention, each indicator comprises an LED preferably centered within one of the tactile sensing keys (i.e. a surface mount LED). These LEDs may comprise a single color LED, preferably red, or multi-color LEDs as desired. In one embodiment, combination red-green LEDs may be utilized which provide a red color output in response to a first polarity and a green color output in response to a second polarity of current flow. The combination LEDs can also output amber tones in response to alternating the polarity. By way of example, this multi-color output may be utilized by configuring a key to provide a tactile stimulus when it outputs green, which when correctly pressed changes to an amber output. Keys not lit up when pressed would be configured to output in red to indicate an error.

An optional general purpose display 24 is preferably provided to display modes of operation, as well as activity statistics, and can be utilized in combination with user inputs for selecting characteristics and settings of the device. Preferably, display 24 comprises a small alpha-numeric or graphical LCD display (i.e. Crystalfontz® part number CFAH1602L or similar), although other forms of display may be utilized. An optional display with touch screen 26 is depicted as controlled through interface 28; which may be utilized in this embodiment or for a programmed tactile I/O embodiment. Some of the feedback information provided by the general purpose display 24 include but are not limited to: a running clock indicating user practice time, instantaneous scores for practice activities and average score values. In addition, the alphanumeric display can be utilized to relay information to the therapist when the system is being operated in an administrative mode.

Right and left sensor bars 30a, 30b are shown interfaced through circuit 32. These extended length sense bars provide a passive restraint means that is configured for sensing that the user is maintaining a specific limb (hand) on the sensing bar when interaction with the opposite limb is being performed.

By way of example, the two sensor bars can be fabricated as wide printed circuit conductor traces etched on a printed circuit board and shaped to conform to the case dimensions. It should also be appreciated that the conductive traces for the bars and keys can also be formed in a number of alternate processes, such as additive processes (i.e. conductive paints, sputtered deposition, etc.) wherein the exterior of a plastic housing can be adapted to provide user input keys, while the LEDs are retained on a printed circuit board within the housing and extending out through holes in the housing. It should be appreciated that methods of fabrication are provided by way of example only, and that one of ordinary skill in the art can create numerous variants in response to the teachings herein without departing from the present invention.

To detect user contact according to one embodiment, the sense bars can be coupled to a very low current proximity sensing control circuit (i.e. two key capacitive touch sensor such as Quantum® part number QT320 or similar) which interfaces with the microcontroller. Contact with the bars provides a signal used to "wake-up" the controller, such as received on an interrupt input of the microcontroller. Receipt of the signal in this case causes the system to turn "ON" as soon as the user touches it. The sensor bars are also used as input devices during normal system operation.

According to one example a limb of the user (i.e. the healthier limb) can be passively restrained by requiring the user to be in constant contact with a specific sensor bar located at the right and left edges of the trainer. The therapist can designate which bar is to be the restraint sensor. The system will function, or register correct responses, only while the designated sensor is being held. If desired, this function can be disabled by the therapist. The sense bar can be configured for sensing contact or pressure from the hand and thumb to ascertain the orientation of the hand as a means of sensing incorrect right-left rotation of the neural training device. Optionally, indicators (i.e. LEDs) may accompany each sense bar for indicating to a patient if either sense bar must be held during the test. For example one or more LEDs (i.e. green) may be positioned along the sense bar. If the user attempts to operate the device without holding the sense bar then this LED can be flashed, and/or the color changed if a bi-color LED is utilized (i.e. flashing red).

Preferably two long sense bars are utilized, one located at each side of the device and preferably wrapping around the upper corner of the neural training device housing. These sense bars can serve three general purposes: (1) utilized to passively "restrain" (without the use of physical restraints) a healthy limb during rehabilitation exercises; (2) utilized as response switches during rehabilitation exercises; and (3) utilized as an "ON" switch for activating the neural training device. An ON switch can be optionally incorporated if desired, such as if the lack of an ON switch may be considered a possible point of confusion for those lacking in short term memory abilities, but which are conditioned to use an ON/OFF switch. An OFF switch is not necessary as the trainer is preferably configured to turn "OFF" automatically following an extended period of inactivity. The device can be configured for activation and deactivation in any manner or by way of a combination of these approaches.

Activation of the unit is preferably accompanied by an annunciation, for example emitting a distinct sound from an audio transducer 34, (i.e. chime tone emitted from a speaker) and activating a visual display element 36 (i.e. green LED) to provide a signal for the hearing impaired. Speaker 34 can be utilized for providing a variety of forms of audible feedback to the user, such as annunciating each key press, a change in mode, incorrect key presses, incorrect orientation of the unit, and so forth. Additional indicators can be supplied as desired for visually indicating these and other conditions for those that are hearing impaired. It should also be appreciated that annunciations can be presented on the general purpose display to aid the hearing impaired.

An accelerometer 38 is operable in one or more axis of motion, such as providing a 1 G maximum range with +/−0.001 G sensitivity (i.e. MEMSIC® Corporation dual axis part number MXR2999EL or similar). In particular the accelerometer is configured for sensing in the X direction to detect if the user is attempting to move the device with the passively restrained limb (i.e. limb which is healthy) to position device buttons beneath a finger of the afflicted limb. The acceleration sensor detects these invalid lateral movements of the trainer that may be caused by moving or thrusting the trainer with the healthy limb instead of reaching out to the proper keys with the afflicted limb. In addition, the accelerometer is preferably configured for sensing in the Y direction to detect if the user is attempting to operate the device with a reversed right-left orientation.

An optional communications interface is preferably provided for communicating with external devices, such as for the downloading of control and patterns, and the uploading of session data from the device to the external device. In this embodiment the communications interface preferably comprises an infrared transmitter-receiver 40 (i.e. Vishay® or Temic® part number TFDS4500 or similar) coupled through interface 42 (i.e. IRDA controller such as Microchip® part number MCP-2150 or similar). The infrared link allows communicating with computers, PDAs, and other devices without the need of establishing a fixed connection. It will be appreciated that any convenient wired or wireless communication mechanism can be utilized without departing from the teachings of the present invention.

Another benefit of the optical communication device is that it can be utilized, preferably in combination with the accelerometer, to provide a means for sensing left-right reversal of the device. This mechanism can thwart attempts by a patient to utilize their more facile hand by rotating the device 1800 wherein the roles of the sensor bars are reversed. By generating light pulses and sensing light reflected from the body of the person using the device, the optical element can generally detect in which direction the device is oriented. If the device is configured for operation in an inclined position, such as with feet or a stand, then acceleration sensing in the Y direction can be unambiguously utilized to determine if the device orientation is reversed left to right.

2. Discrete I/O Embodiment.

Figure 2:
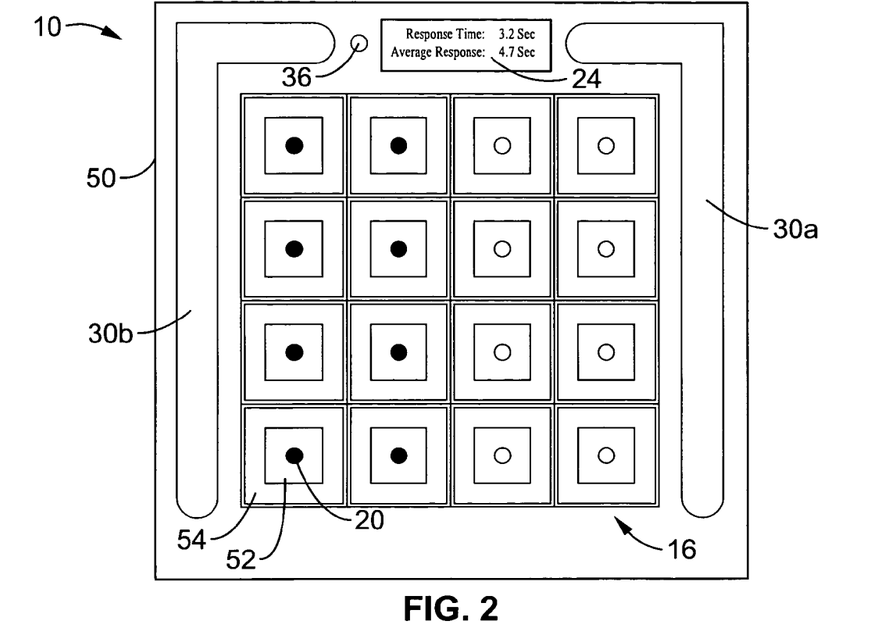
FIG. 2 is a top view of a neural training device according to an embodiment of the invention, showing a square array of 16 accuracy sensitive tactile inputs, along with bar sensors and text/graphic display.

FIG. 2 illustrates by way of example a discrete I/O implementation 10 of the neural trainer. A square array of sixteen tactile area inputs 16 are shown each having a center tactile region 52 and an outer tactile ring portion 54 surrounding each center region. In this embodiment the total of thirty two touch sensitive keys consist of sixteen large keys, such as measuring about 2½ inches square, arranged in a 10 inch by 10 inch square 4×4 matrix. Each of the large keys contains a smaller, secondary, key centered within it. Each of the sixteen smaller keys in this example embodiment measures about 1½ inches square. All keys can be configured to provide any desired form of detection. In one preferred embodiment the keys are configured for proximity sensing wherein no moving parts are required which simplifies the mounting and connections to the centralized LED on each key.

A separate light emitting diode (LED) indicator is provided in this embodiment for each of the smaller keys for generating a visual stimulus pattern for the user to act upon. One LED is preferably located at about the center of each key. The activity on the keys is registered by an embedded microcontroller, such as through a keyboard interface circuit. The keys may be independently connected or configured in one or more row-column arrays. For example using a separate 4×4 row-column array for detecting activity in the set of center keys, and separately for the surrounding keys.

Programming on the neural training device is configured so that a number of keys can be combined and treated as a single key to support lower skill levels. This technique allows the neural-trainer device to interactively adjust key size to match the capabilities of the user. The smallest key in this embodiment is about 1½ inches square and the largest key, provided when all keys are connected together, is a 10 inch square. User feedback messages for this embodiment are provided on an alphanumeric display, such as having sixteen character positions in each of two rows.

The neural-trainer device provides a stimulus to the user via the stimulus annunciators, preferably comprising the sixteen LED matrix coupled to the keys. In operation, the controller updates the state of these key indicators. In similar manner to the keypad inputs, the LEDs may be individually coupled to a driver, or coupled in a row-column arrangement. In a preferred embodiment, the LED driver interface can enter a low-power, or "sleep" mode, when the high intensity displays are not required, thus reducing operating current.

The diagrams for the operation of the neural-trainer device depict an embodiment with discrete keys, however, programmed tactile I/O embodiments may be alternatively utilized.

3. Programmed I/O Embodiment.

Another embodiment of the invention utilizes a touch sensitive display screen (monochrome or color) which can simulate the operation of the discrete I/O embodiment described above. For example a 10"×10" touch sensitive display (or other desired display form factor) can be utilized which is manufactured according to any convenient and preferably low-cost display technology, including but not limited to liquid crystal display (LCD), electronic ink (EInk), electroluminescent (EL), or organic LED (OLED). The outline of the keys are displayed on the panel and correlated with touch contacts on the screen. It should be appreciated that the size and number of keys displayed on the touch-screen embodiment can be selected by neural training device programming in response to the type or level of training being performed. For example, sixteen keys may be utilized for conventional training while fewer keys can be provided for those with severe problems, or additional keys utilized for those with less disability.

It should also be appreciated that the added flexibility of the touch screen allows the background to be changed, the location and relationships of the keys to be changed, and allows the stimulus to be provided in a number of alternative ways. By way of example in some applications it may be beneficial for the patient to discern the stimulus which is overlaid over a background image. The stimulus may for example comprise a section of the display shown shaded, as inverse video, outlined and so forth. By way of another example, the stimulus and/or response key may be in the form of animals or other simple shapes that would be user friendly to younger patients. It will be appreciated that the flexibility of the application can be more readily extended utilizing the programmatic I/O embodiment.

Furthermore, it should be understood that the neural training device can be implemented according to the invention as a dedicated, embedded system, device, or it may comprise programming (with optional hardware) for executing on a general purpose computing device, such as a tablet PC or other device configured with a touch sensitive screen.

4. Administrative Operating Mode.

This embodiment of the neural training device provides one administrative mode, in which access is limited to the therapist or other authorities, and four user modes of operation including "Responsive Mode", "Predictive Mode", "Visual Perception Mode" and "Multi-tasking Mode".

According to one mode of operation, the therapist accesses the Administrative Mode by pressing a unique sequence of keys on the keyboard. In this mode, the therapist can tailor the operational characteristics of the trainer to match the needs of the patient. When in user modes, the trainer device continually monitors user performance and stores results in memory. The stored data is available to the therapist for use as a tool in the evaluation of user progress, such as measured over a long time period. The therapist can access the data via the alphanumeric display on the trainer device. In addition, the stored data can be optionally uploaded to another device, such as a pocket PC or Personal Data Assistant (PDA), via an infrared or other communications link; where it can be analyzed and printed in the form of a graph or data table. In one embodiment, the device can be configured with a network interface (wired LAN, wired phone-based modem, WiFi, other wireless formats) to allow it to establish connectivity with remote systems over a local network, or more preferably over the Internet. It will be appreciated that many microcontroller boards are available which provide resident Internet connectivity with associated programming modules, such as manufactured by Rabbit Semiconductor® of Davis, Calif.

It will be appreciated that the administration mode can generate a wide variety of statistics for ascertaining strengths and weaknesses of a patient using the device. One of those statistics involves determining spatial relationship with tactile responses. In one example of this, keys are electronically grouped into four blocks of four keys each and the programming calculates and records data representing response times for each of the four quadrants on the keyboard, or even specific to smaller areas or even to each specific key. The recorded data represents the average of all responses in each quadrant, taken over an extended period of time. The operation of this, and other, user tactile characterization functions is not apparent to the user as it is a background processing function. However, this data made available to the therapist provides a valuable indicator that can be utilized to help identify undetected problems with visual perception.

The administrative mode can provide a wealth of valuable information to the administrator. By way of example, some of the data that can be made available to the therapist in this mode include, but are not limited to:

(1) Total cumulative practice time for the patient.
(2) Total number of practice sessions.
(3) Skill level achievements.
(4) Average response time for all responses.
(5) Average response time for each of the four quadrants.
(6) Average score for precision of hand movement.

The administrative mode will also allow the therapist to customize the operational characteristics of the trainer. By way of example, some of the characteristics that can be customized include, but are not limited to:

(1) Selection of which sensor bar will be used to "immobilize" one limb of the patient, such as the more healthy limb. The choices may comprise: Left, Right, Alternating, Random, or None.

(2) Selection of the mode of operation. The choices are: Responsive, Visual Perception, Predictive, or Multi-task mode.

(3) Initialization of the communications link between the neural training device and another system, such as a personal computer or PDA. This interface is used to transfer data from the trainer into another computer, network, or similar device.

5. Overview of User Operating Modes.

This embodiment of the neural training device is configured with modes of user interaction comprising a "Responsive Mode", "Predictive Mode", "Visual Perception Mode" and "Multi-tasking Mode". Each of the user modes addresses a different type of neurological impairment or learning disorder. Evaluation and rehabilitation capabilities are provided in each of the four modes.

6. Responsive Operating Mode.

Figure 3:
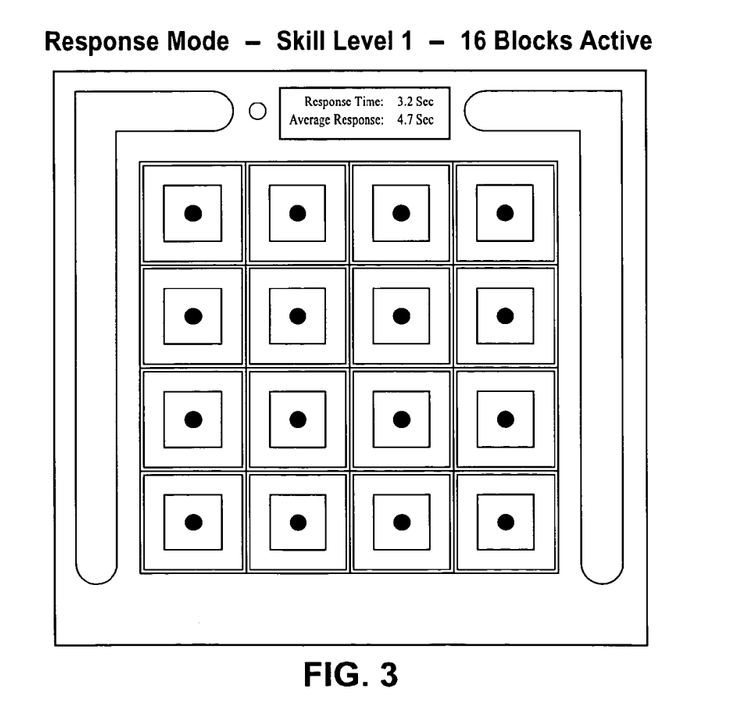
FIG. 3-10 are top views of the neural training device of FIG. 2, illustrating skill levels and example operation within a responsive mode.
Figure 4:
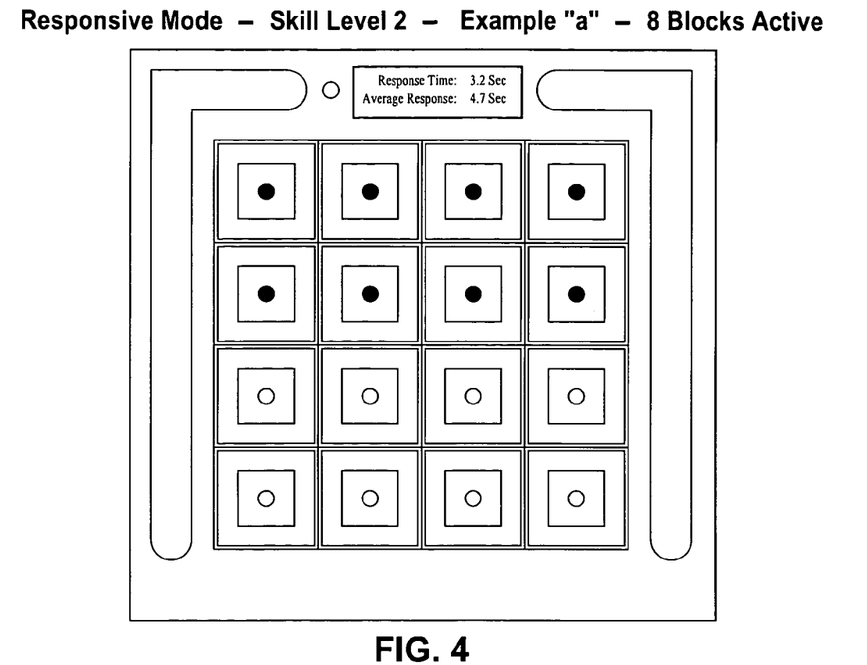
Figure 5:
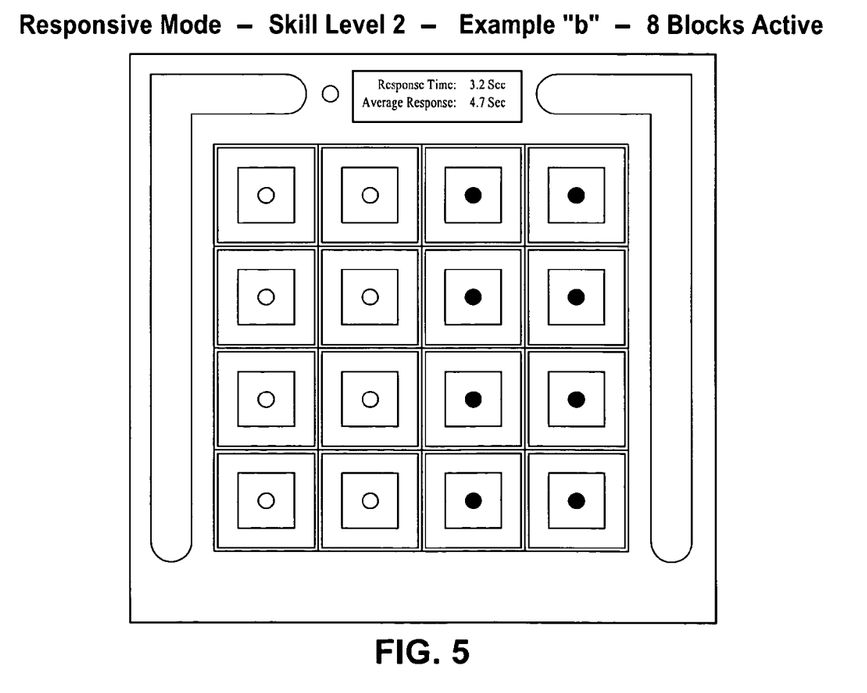
Figure 6:
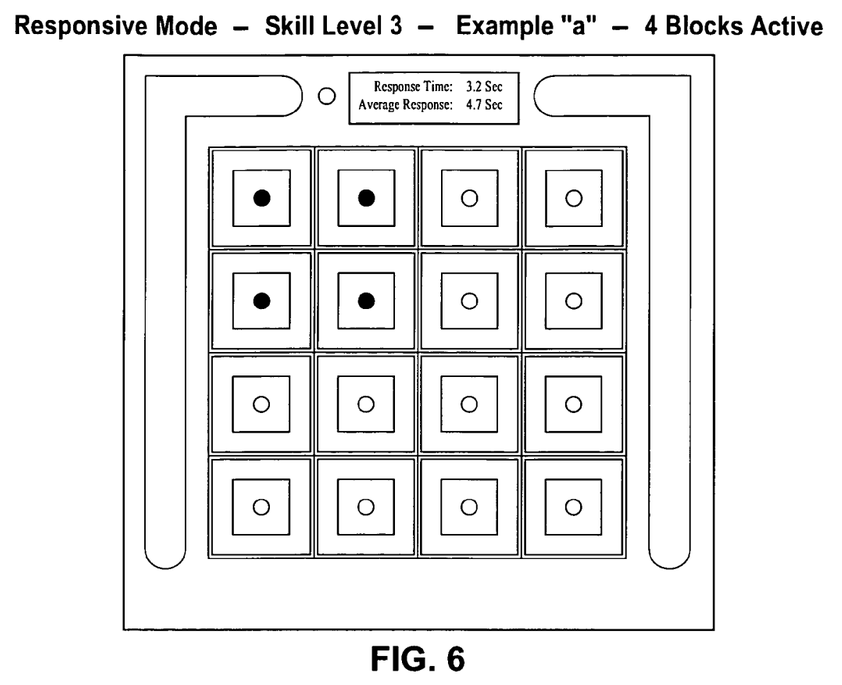
Figure 7:
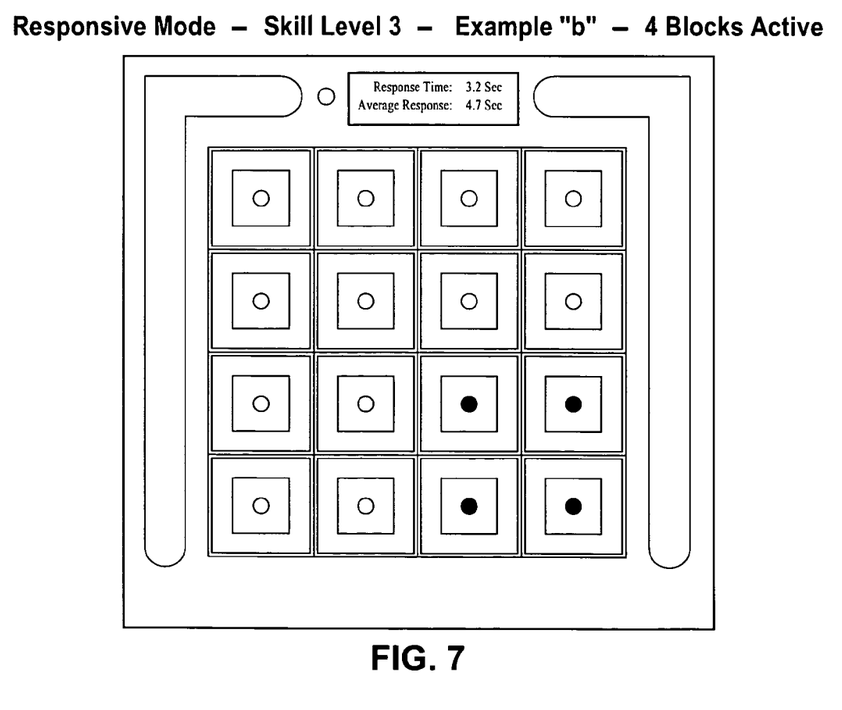
Figure 8:
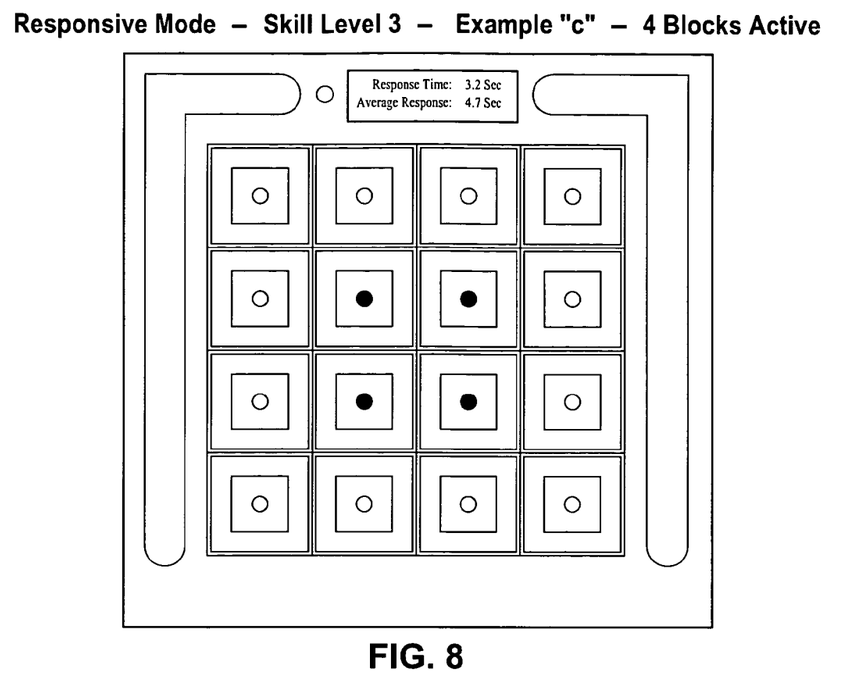
Figure 9:
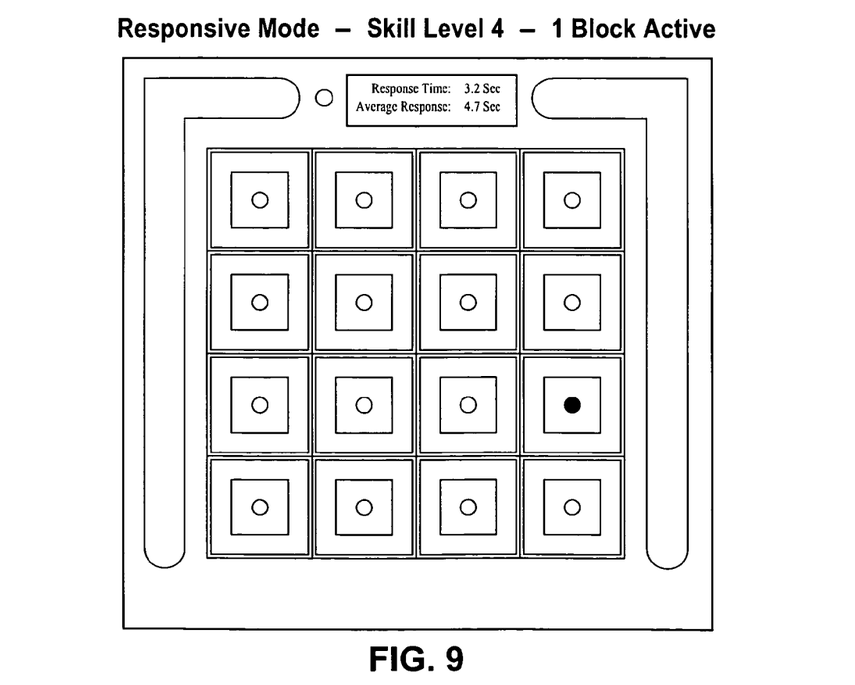
Figure 10:
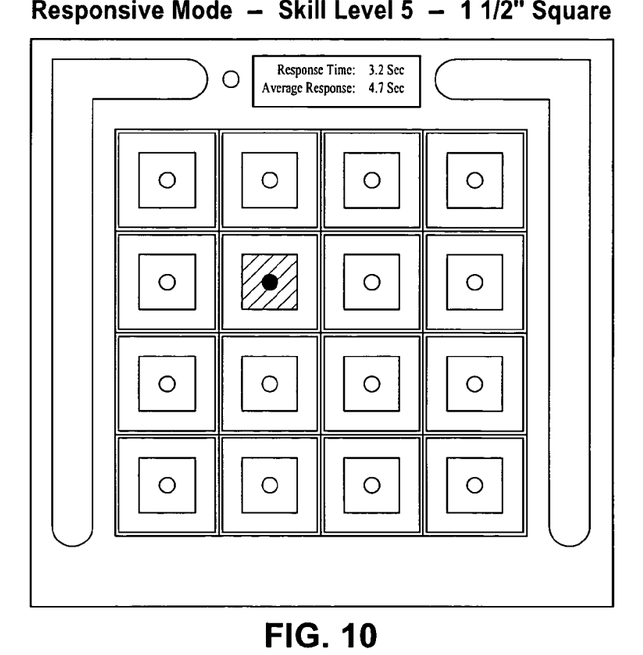
Figure 11:
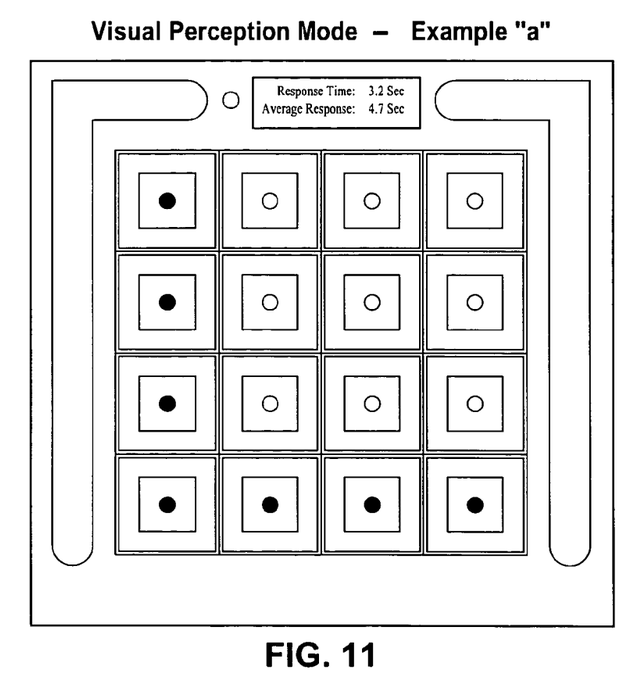
FIG. 11-14 are top views of the neural training device of FIG. 2, illustrating skill levels and example operation within a visual perception mode.
Figure 12:
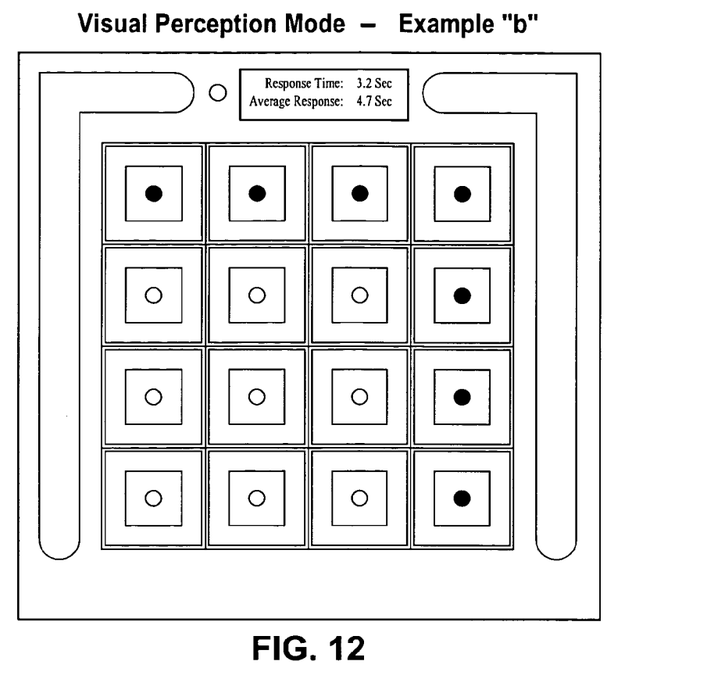
Figure 13:
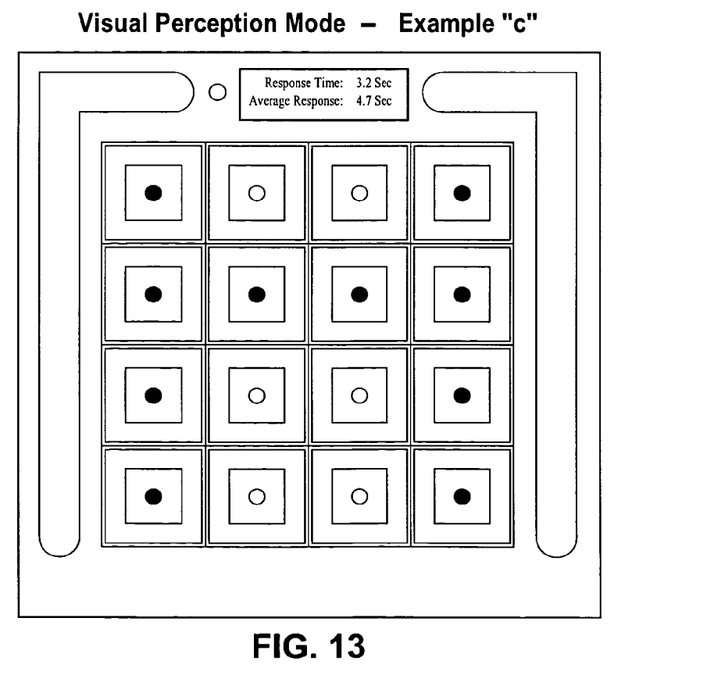
Figure 14:
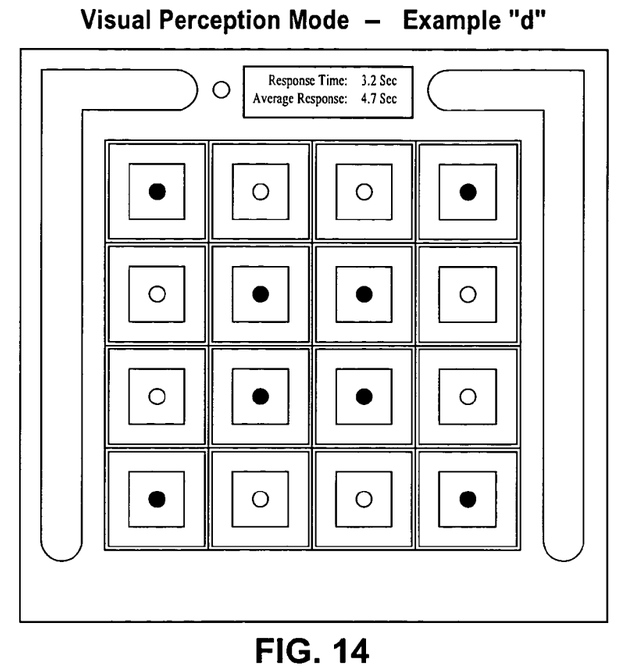

FIG. 3 through 10 illustrate different target patterns according to five skill levels of this embodiment of the Responsive Mode. FIG. 3 depicts the lowest skill level (Skill Level 1) in which all indicators are illuminated to stimulate a tactile response anywhere in the block of keys. FIG. 4 and FIG. 5 depict examples of a second skill level (Skill Level 2) in which eight of the indicators are illuminated, such as at the top portion (FIG. 4), right portion (FIG. 5), bottom portion, or left portion of the group of keys. FIG. 6, FIG. 7, and FIG. 8 depict a third skill level (Skill Level 3) in which the tactile stimulus comprises a four key group shown at assorted positions on the device. FIG. 9 depicts a fourth skill level (Skill Level 4) in which a single key is illuminated including both inner and outer area, accuracy penalties arise for pressing adjacent keys. FIG. 10 depicts a fifth skill level (Skill Level 5) in which only the center portion of the key is active, wherein contact with the outer portion of the key or adjacent keys triggers accuracy deductions.

The objective of the Responsive Mode is to provide goal-directed activities designed to help promote repetitive, well-focused use of an impaired limb. In this mode, a stimulus is provided by a random illuminated target on the trainer surface. The user responds by touching the illuminated target as quickly and precisely as possible. The system measures the response time of the user and preferably the precision of their tactile response during target acquisition. Following target acquisition the illuminated target stimulus is deactivated and the response scores updated. Preferably, a running average is generated with preceding response scores and displayed. Once the user acquires the first target a subsequent target can be immediately illuminated, or illuminated after a desired delay period. The measurement sequence is preferably repeated for the duration of the testing period.

The precision of tactile feedback is a measure of how accurately the target key is touched without first touching an adjacent key, or keys, or a ring about the exterior of the central key in skill level 5. Any contact other than the target area will result in a lower score for accuracy (precision). In addition, the accuracy deductions are preferably weighted in response to the distance that the erroneous key touch is from the target key. Consequently, touching keys furthest from the target key will yield the lowest score for precision. It should be appreciated that in lower skill levels (i.e. Skill Levels 1-3) a number of keys are grouped to create a "super-key", in which any contact within the elements of the super-key is a hit, while contacting keys not identified in the super-key set would constitute a miss.

The adjusted response time comprises the actual response time that has been mathematically adjusted according to the precision with which the target was acquired. A lower score for precision will result in an increased score for adjusted response time, representing a longer time to acquire the target.

The objective of the test is to achieve a low adjusted response time score, indicating a quick and precise reaction. Slower responses and poor precision will result in higher score values. Under no circumstances should the user be discouraged by receiving an extremely high score for poor performance. It is preferred, therefore, that the displayed score never exceed 120 seconds, even for users with very slow, or inaccurate, responses. The actual score is retained in memory for use by the technologist.

Positive feedback is preferably provided by a blinking LED and a chime that sounds each time the acquisition time for a response is less than the average time for preceding responses.

During operation, neural training device programming optimizes the challenge level during each exercise session by continuously monitoring and responding to user progress. The logic interactively increases or decreases the size of the key/target and skill level as appropriate. By continuously maintaining this optimum level of challenge, maximum benefit can be achieved from each exercise session while reducing the possibility that the user will become either bored or frustrated. Therefore, maximum benefit is derived by minimizing the use of skill levels that are either too simple or too complex.

For example, the programming can be configured to interactively adjust the target size in five steps from a 10 inch square target (Skill Level 1) down to a 1½ inch square (Skill Level 5.) As the skill level becomes more challenging, the target gets smaller and moves randomly about the surface of the trainer.

7. Visual Perception Operating Mode.

FIG. 11 through FIG. 14 illustrate different examples of the Visual Perception operating mode. Examples of different visual perception patterns are shown in FIG. 11 through FIG. 14 for collecting multiple user inputs in response to multiple stimuli. Visual patterns preferably cross from an area of good vision into an area of poor vision.

The objective of this mode is to provide exercises that can help a user compensate or overcome deficiencies with visual perception in an area within their field of vision. This loss of visual perception can be in the left or right half, or in the upper or lower half of the field of vision.

In the Visual Perception Mode, a pattern of target squares is illuminated. The light patterns are designed to lead the user from an area on the board where visual perception is not a problem into an area where the user is experiencing difficulties. Hence, the pattern may lead from one side of the board to the other, from top to bottom or diagonally. As the user touches each of the illuminated squares, the corresponding light in that square is extinguished and a "click" is preferably sounded to reinforce that an illuminated target square has been successfully identified and touched. After all of the illuminated squares have been touched, and all target lights finally extinguished, a light will blink and a "chime" tone will be sounded. Target squares located within the area of better vision will most probably be identified first, but the user will not be awarded the "chime" tone until all squares have been identified and touched. A score will be displayed.

8. Predictive Operating Mode.

Figure 15:
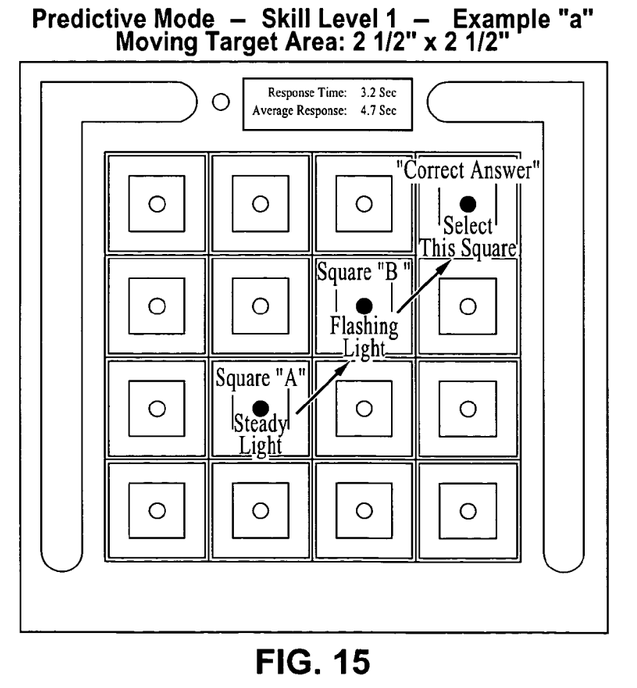
FIG. 15-16 are top views of the neural training device of FIG. 2, illustrating skill levels and example operation within a predictive mode.
Figure 16:
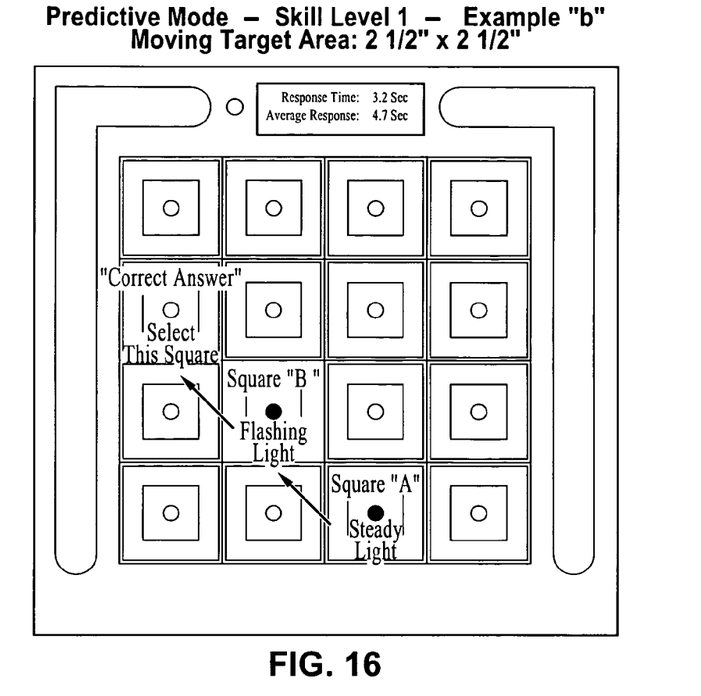

FIG. 15 and FIG. 16 illustrate different examples of the Predictive operating mode. The objective of this mode is to provide exercises that help the user develop reasoning skills by predicting a simple sequence of events. In this mode, two adjacent target squares are illuminated. One square is illuminated continuously while the other square flashes at one second intervals. The user must predict where the next (third) target would have been illuminated (in line with the two illuminated squares and directly adjacent to the flashing square.) The user selects a square by touching it. If the correct square is touched, a light will blink, a chime will sound and a score will be displayed. Following a short pause, a new problem (sequence of lights) will be presented. If an extraordinary period of time elapses before a square is touched, or if an incorrect square is touched a light will blink and a "click" will be sounded. The original light sequence will be repeated to prompt the user for one more try. If two consecutive answers are incorrect, the light pattern will again be repeated and the "answer" square will flash slowly to direct the user to the correct answer. After the user touches the correct square, a light will blink and a chime will sound. Following a short pause, a new problem (light pattern) will be presented.

9. Multi-tasking Operating Mode.

The objective of this mode is to provide exercises that help the user develop multi-tasking skills preferably involving both limbs. In this mode, the user will use the right hand to contact and hold any illuminated key which is located on the right side of the keyboard, as illustrated by the eight shaded keys in FIG. 17. Similarly, the user will use the left hand to contact and hold any illuminated key which is located on the left side of the keyboard, as illustrated by the eight keys, in FIG. 17, that are not shaded. Contact will be maintained with a key as long as it remains illuminated. When no key is illuminated on either the right or on the left side of the keyboard, the corresponding hand will contact and hold the adjacent sense bar. Preferably the position of the illuminated keys will change randomly. Furthermore, changes on the right side of the keyboard will be independent from those on the left side of the keyboard. Alternatively, lower skill levels can be provided as desired by illuminating blocks of keys on each side for response and by using a slower rate of change for the illuminated keys. Higher skill levels can be achieved by using single keys and by increasing the rate of change for the illuminated keys.

Figure 17:
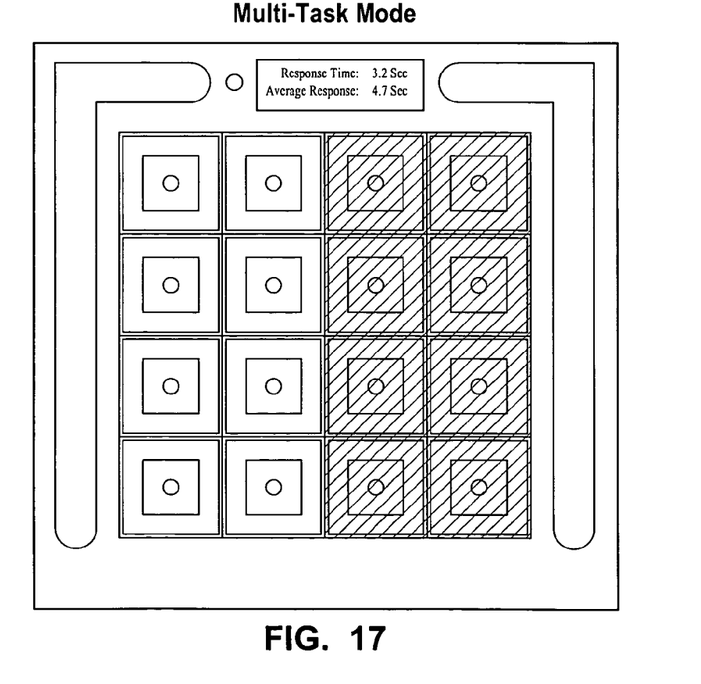
FIG. 17 is a top view of the neural training device of FIG. 2, illustrating operation within a multi-task mode.

This operating mode requires user interaction from either the right or left side, or both. Key conditions for the right hand and left hands will change independently from each other, according to a pattern or randomly. A user score will be calculated based upon the response time and accuracy of both hands.

10. Optional Device Aspects.

The keys of the neural training device are generally described as being non-tactile keys, wherein a mechanical displacement is not necessary for activating a key press on a key. However, the invention may be embodied with keys requiring a depth of travel for activation. A key which is subject to a sufficient level of travel before it registers a key-press can provide a mechanism to force the operator to extend a finger for pressing the key, wherein they will be unable to keep the hand in a static position and just contact a portion of the hand to a key on the device.

It should also be appreciated that accuracy can be sensed by configuring a set of keys to separately register both casual contact (error) and a proper tactile key click. The casual contact is registered whenever the user makes any contact with the key top, even if the key is not depressed. The tactile key click only occurs when the user presses the key and moves it through a sufficient travel (or alternatively past a sufficient pressure threshold level) to be registered as a key click. In this embodiment the keys of the device need not utilize inner keys with outer rings as the surrounding keys provide the casual contact sensing which is provided by the outer rings. The casual contact and key click sensing are preferably independent wherein both casual contact and a key click can be simultaneously registered.

By way of example the dual sense single area key can be implemented with a conductive key top connected for proximity sensing used in combination with a means for detecting sufficient key travel (i.e. mechanical switch, snap dome, tactile response capacitive or inductive response key, and so forth). In this way proximity sensing can detect subtle contact for generating signals used for assessing accuracy penalties, without interfering with sensing keys which are being pressed through their stroke to activation.

In another alternative embodiment, the neural training device of the present invention can be adapted to provide for the selective exercising of all the fingers of the hand of the user by incorporating a tactile glove mechanism, or other means of detecting which fingers of the hand are utilized for operating the various keys. In one preferred embodiment the glove circuit is coupled to the trainer through electrical wiring connected to a receptacle, however the glove can be configured to communicate wirelessly, such as utilizing a small battery, passive RFID techniques, and so forth. The glove is preferably fabricated from a light-weight breathable material (i.e. cotton, or thin mesh glove), configured with a tactile sensor at the tip of each glove finger so that the device can detect which finger was used for pressing the given key. The sensor at the tip preferably comprises one or more simple contact switches to detect that contact pressure has been applied. The neural training device according to this embodiment is preferably configured for indicating which finger is to be utilized for a given exercise or motor response step within that exercise. For example the glove can be configured with indicators (i.e. surface mount LEDs, or organic LEDs) which direct the user as to which finger is to be used. Alternatively, the user can be directed as to which finger to utilize by generating an audio annunciation, or more preferably by displaying a graphic which highlights the finger to be used (i.e. on the general purpose display). In this way the device can aid the user in rehabilitating the use of all fingers, not just the one finger that they have the most control over. The physical therapist, or other rehabilitation practitioner, can establish if and how finger selection control would be utilized on the device.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for assisting in the evaluation and rehabilitation of an individual having a neurological impairment, comprising:
    (a) a touch pad having a plurality of primary touch sensitive keys arranged in a matrix;
    (b) a secondary touch sensitive key positioned in the approximate center of each primary touch sensitive key;
    (c) a visual stimulus emitting source positioned in the approximate center of each said secondary touch sensitive key upon which user tactile response is to be directed;
    (d) a microprocessor and memory for storing executable programming; and
    (e) programming associated with said microprocessor for carrying out the operations of
        (i) providing visual stimuli to a user,
        (ii) monitoring position and timing of user tactile feedback in response to said visual stimuli, and lowering registered positional accuracy of tactile feedback in response to detecting user contact with the primary touch sensitive key when responding to the visual stimuli on said secondary touch-sensitive key, and from which incorrect tactile feedback is distinguished in response to detecting user contact outside of either the secondary or primary touch sensitive key,
        (iii) controlling presentation of said visual stimuli to the user and for processing said tactile feedback.

2. An apparatus as recited in claim 1, further comprising means for passively restraining a limb to restrict which limb user tactile feedback will be collected.

3. An apparatus as recited in claim 1, further comprising programming for carrying out the operations of:
    generating one or more patterns of visual stimuli;
    enabling one or more of said touch sensitive keys to be responsive to tactile feedback from the user in response to said visual stimuli; and
    altering the number and position of said touch sensitive keys which are responsive to tactile feedback from the user.

4. An apparatus as recited in claim 1, further comprising programming for supporting an administrator mode in which access is provided to performance statistics and for establishing device operating characteristics.

5. An apparatus as recited in claim 4, wherein said administrative mode programming is configured for providing access to said programming in said microprocessor for controlling operation of said apparatus.

6. An apparatus as recited in claim 1, further comprising programming for providing a responsive mode in which the user provides a tactile response to each visual stimuli.

7. An apparatus as recited in claim 6, wherein said responsive mode comprises:
    providing said visual stimuli;
    measuring response time and positional precision of the user's tactile feedback; and
    adjusting the number and position of said touch sensitive keys based on said response time and precision of user tactile feedback.

8. An apparatus as recited in claim 1, further comprising programming for providing a predictive mode in which response to the stimuli requires the user to extend a sequence.

9. An apparatus as recited in claim 8, wherein said predictive mode comprises:
    illuminating first and second adjacent touch sensitive keys, each said key having a light emitting source position in the approximate center thereof, wherein a said one of said light emitting sources is illuminated continuously, and wherein an adjacent said one of said light emitting sources is illuminated intermittently;
    receiving tactile feedback from the user in response to said illumination of said first and second adjacent touch sensitive keys; and
    providing audible feedback to the user if the user touches a touch sensitive key adjacent to said intermittently illuminated touch sensitive key.

10. An apparatus as recited in claim 1, further comprising programming for providing a visual perception mode in which multiple user inputs are required across a span of visual stimuli.

11. An apparatus as recited in claim 10, wherein said visual perception mode comprises:
    providing said visual stimuli;
    receiving said tactile feedback from the user; and
    providing a first type of audible feedback to the user in response to receiving said tactile feedback from the user; and
    providing a second type of audible feedback to the user in response to receiving said tactile feedback from the user;
    wherein said first type of audible feedback is provided in response to tactile feedback applied to individual touch keys; and
    wherein said second type of audible feedback is provided in response to tactile feedback applied to a predetermined number of said touch keys.

* * * * *